(12) United States Patent
McCullagh et al.

(10) Patent No.: US 7,311,031 B2
(45) Date of Patent: Dec. 25, 2007

(54) BRAIDED STENT AND METHOD FOR ITS MANUFACTURE

(75) Inventors: Orla McCullagh, Waltham, MA (US); William R. Quinn, Swampscott, MA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 11/657,864

(22) Filed: Jan. 25, 2007

(65) Prior Publication Data

US 2007/0119295 A1 May 31, 2007

Related U.S. Application Data

(60) Continuation of application No. 11/294,287, filed on Dec. 5, 2002, now Pat. No. 7,213,495, which is a division of application No. 10/295,454, filed on Nov. 15, 2002, now Pat. No. 7,001,425.

(51) Int. Cl.
*D04C 1/06* (2006.01)
(52) U.S. Cl. .................................. 87/8; 87/13
(58) Field of Classification Search ............ 87/5, 87/7–9, 11, 13
See application file for complete search history.

(56) References Cited

U.S. PATENT DOCUMENTS

| | | | |
|---|---|---|---|
| 2,093,838 A | 9/1937 | Kellems | |
| 6,161,399 A | 12/2000 | Jayaraman | |
| 6,241,757 B1 | 6/2001 | An et al. | |
| 6,398,807 B1 | 6/2002 | Chouinard et al. | |
| 6,443,186 B1 | 9/2002 | De Meyer et al. | |
| 6,585,758 B1 | 7/2003 | Chouinard et al. | |
| 6,622,604 B1 | 9/2003 | Chouinard et al. | |
| 6,719,934 B2 | 4/2004 | Stinson | |
| 2001/0029398 A1 | 10/2001 | Jadhav | |
| 2001/0056299 A1 | 12/2001 | Thompson | |
| 2003/0153973 A1 | 8/2003 | Soun et al. | |

FOREIGN PATENT DOCUMENTS

EP  0 775 471  5/1997

(Continued)

OTHER PUBLICATIONS

International Search Report of International Application No. PCT/US03/33409 dated Mar. 17, 2004.

*Primary Examiner*—Shaun R. Hurley
(74) *Attorney, Agent, or Firm*—Hoffmann & Baron, LLP

(57) ABSTRACT

A stent includes regions of differing numbers of braided filaments to provide different dimensions and/or properties in different regions along the stent length. The stent may include a first and second plurality of braided filaments each braided together. The second plurality of braided filaments is braided into the first plurality of braided filaments to form a region of different properties than the first. A method of constructing a braided stent includes the steps of braiding a first plurality of filaments to form the flexible portion, combining a second plurality of filaments to the first plurality of filaments, and then braiding the second plurality of filaments with the first plurality of filaments to form the more rigid region from the combination of the first and second plurality of filaments, where the second plurality of filaments is braided only in the rigid region.

21 Claims, 5 Drawing Sheets

FOREIGN PATENT DOCUMENTS

| | | | | | |
|---|---|---|---|---|---|
| WO | WO 95/17859 | 7/1995 | WO | WO 00/44309 | 3/2000 |
| WO | WO 96/25124 | 8/1996 | WO | WO 01 35864 | 5/2001 |
| WO | WO 99 44540 | 9/1999 | WO | WO 01 54621 | 8/2001 |
| | | | WO | WO 01 54622 | 8/2001 |

BRAIDED STENT AND METHOD FOR ITS MANUFACTURE

CROSS-REFERENCE

This application is a continuation of application Ser. No. 11/294,287, filed Dec. 5, 2002, now U.S. Pat. No. 7,213,495, which is a divisional of application Ser. No. 10/295,454, filed Nov. 15, 2002, now U.S. Pat. No. 7,001,425, which are incorporated herein by reference in their entirety and for all purposes.

TECHNICAL FIELD

This invention relates generaly to stents and stent-grafts, and more specifically, to braided stents and stent-grafts having segments of different strength and rigidity along the length, and/or different diameters of varying or constant strentgh and rigidity along the length.

BACKGROUND OF THE INVENTION

A stent is an elongated device used to support a luminal wall. A stent, along with a graft cover or liner, together provide an unobstructed conduit for fluid flow in the area of a stenosis. Such a stent-graft would typically have a tubular graft layer covering, or lining, the inside or outside of the stent (or both), thus providing a fluid conduit to bypass a stenosis or otherwise diseased body passageway.

Various types of stent architectures are known in the art, including many designs comprising a filament or number of filaments, such as a wire or wires, wound or braided into a particular configuration. Included among these wire stent configurations are braided stents, such as is described in U.S. Pat. No. 4,655,771 to Hans I. Wallsten and incorporated herein by reference. The Wallsten patent is only one example of the many variations of braided stents known in the art and thus is not intended to be a limitation of the invention described herein later. Braided stents tend to be very flexible, having the ability to be placed in tortuous anatomy and still maintain patency. The flexibility of braided stents make them particularly well-suited for use in intraluminal delivery where the lumen of the vessel becomes contorted and irregular both before and after placement of the stent.

The most common use of stents and stent-grafts is in the vascular system, in which stents and stent-grafts having a first small diameter compressed configuration may be introduced into a body lumen at a point remote from a site in that lumen in need of repair and then transported through that lumen, typically through a catheter, to that site. Once the site in need of repair is reached, the stent or stent-graft is either expanded or allowed to expand to a second, expanded configuration to provide an open passageway through that site.

Many of these braided stents have the problem, however, of either being too rigid such that intraluminal delivery and placement becomes difficult, or too flexible (at the cost of reducing radial strength) such that radial expansion forces exhibited at the site of treatment are insufficient to adequately maintain an open passageway through the site. Moreover, by increasing the radial strength of a stent, one typically reduces flexibility, because the stent is more rigid. Likewise, by increasing flexibility, radial strength is often sacrificed.

Thus, there is still a need to provide a fully-supported stent-graft that is flexible enough for navigation through tortuous lumina but rigid enough to properly anchor the device and maintain patency through the device at the site of treatment.

SUMMARY OF THE INVENTION

The present invention provides a stent having segments of different strength and rigidity, or other differential properties, along its length, and/or different diameters of varying or constant properties along its length. In one embodiment of the invention, the diameter along the length of the stent is constant, but the rigidity of the stent changes along the longitudinal axis. In another embodiment, the rigidity of the stent stays the same along the longitudinal length, but the diameter changes. In still yet another embodiment, both rigidity and diameter change along the length of the stent. This variance in diameter and/or radial strength or rigidity is achieved through the use of different numbers of filaments braided into the stent at different locations. Generally, where more rigidity, or the same rigidity with a larger diameter, is desired, more filaments are added.

More specifically, and in a preferred embodiment, the stent of the present invention has a first plurality of braided filaments in one region, and an additional plurality of filaments added to the first plurality of filaments which are together braided to form a second region. The second plurality of filaments are present only in the second region. A preferred embodiment comprises a stent having a narrow region and a broader region with the broader region comprising more filaments than the narrow region such that increased radial strength is exhibited in the broader region. A more preferred stent of the present invention has a first plurality of filaments extending throughout the narrow region and the broader region, and a second plurality of filaments extending along only the broader region. The second plurality of filaments is preferably braided into the first plurality of filaments. In a still yet more preferred embodiment, the stent further comprises a transition region between the narrow region and the broader region. The transition region is comprised of the first plurality of filaments whose braiding increases in diameter from the narrow region to the broader region.

Also included in the invention is a method of braiding a stent having a region of relatively greater flexibility and a region of relatively higher radial strength. The method includes the steps of first braiding a first plurality of filaments to form the more flexible region, and then adding a second plurality of filaments to the first plurality and together braiding the combination to form the more rigid region of the stent. The method preferably includes the steps of first braiding a first plurality of filaments to form a narrow region, then combining a second plurality of filaments to the first portion, and braiding the second plurality of filaments with the first plurality of filaments to form a broader region from the combination of the first and second plurality of filaments. The method preferably includes braiding the stent around a mandrel having a mandrel body comprised of a first portion and a second portion, wherein the first step comprises braiding the first plurality of filaments about the first mandrel portion, and the last step comprises braiding the second plurality of filaments combined with the first plurality of filaments about the second mandrel portion. The second plurality of filaments are present only in the more rigid region. The second mandrel portion preferably has a larger diameter than the first mandrel portion.

An optional, but preferred feature of the invention, is the provision of atraumatic termination to the braided stent structure, both at the stent ends and at the mid-stent locations where one plurality of braided filaments ends.

BRIEF DESCRIPTION OF DRAWINGS

The invention is best understood from the following detailed description when read in connection with the accompanying drawings. It is emphasized that, according to common practice, some of the features of the drawings are not to scale. On the contrary, the dimensions of some of the features are arbitrarily expanded or reduced for clarity. Included in the drawing are the following figures.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Figure 1A:
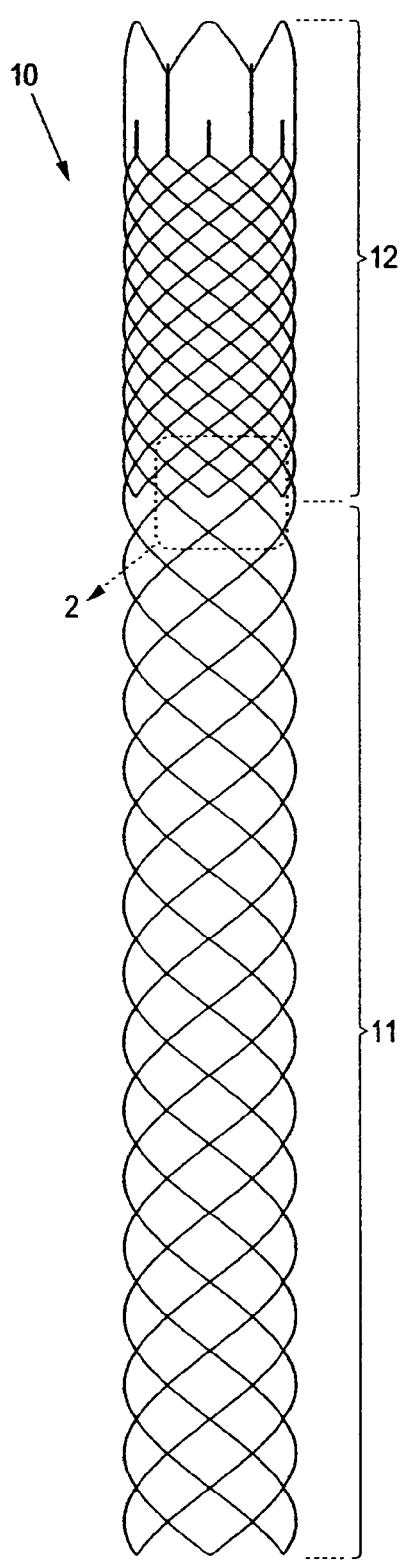
FIG. 1A is a side view of a stent according to the present invention having a constant radius.

Referring to FIG. 1A, there is shown a braided stent 10 according to the present invention. For purposes of this invention, a braided stent is one formed by at least two sets of parallel continuous filaments, the two sets traversing the circumference of the stent in lengthwise but angularly intersecting directions. The two sets of filaments are interlaced or interwoven to form a tubular, supportive structure. The stent shown in FIG. 1A comprises a relatively flexible region 11 and a relatively rigid region 12 (having greater radial strength than flexible region 11). Rigid region 12 comprises more filaments than flexible region 11 and therefore exhibits greater radial strength. In one embodiment (and as shown in FIG. 1A), the number of filaments in rigid region 12 is twice that of flexible region 11. A stent as shown in FIG. 1A can be braided on a mandrel (not shown) using the method described in detail below.

Figure 1B:
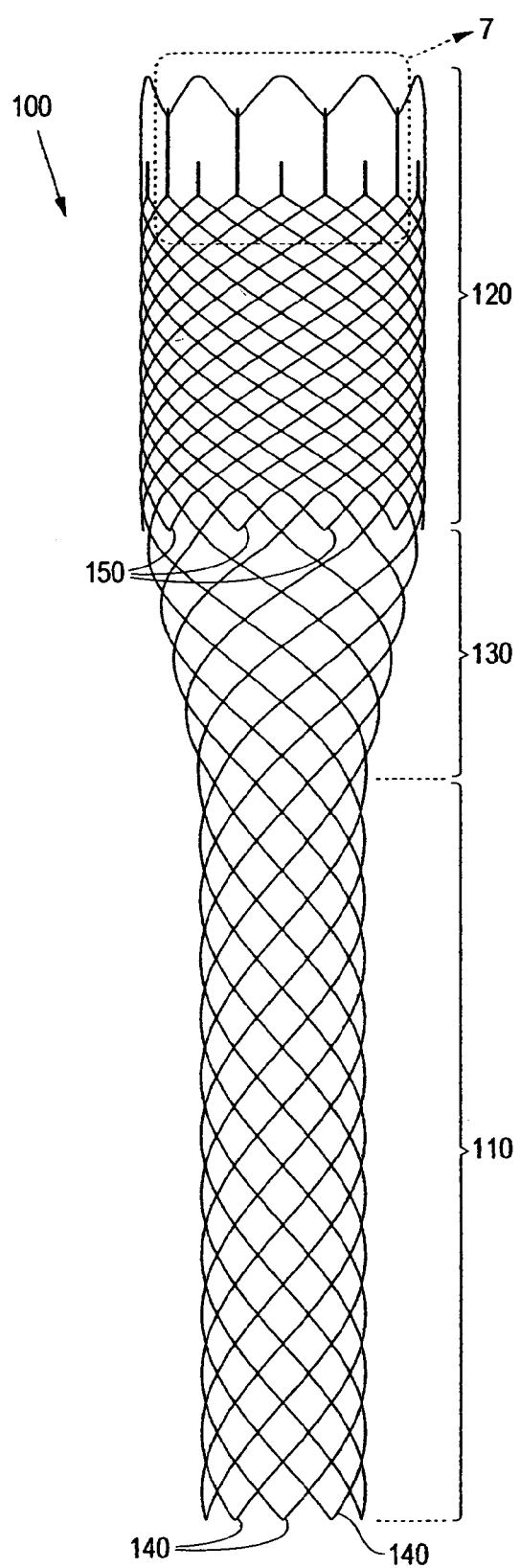
FIG. 1B is a side view of a stent according to the present invention having a narrow region and a broader region.

Referring now to FIG. 1B, there is shown a braided stent 100 according to the present invention. As shown in FIG. 1B, the stent comprises a narrow (or smaller diameter) region 110 defining a first lumen comprised of a first plurality of filaments, and a broader (or larger diameter) region 120 defining a larger lumen than said first lumen. Broader region 120 is comprised of the plurality of filaments from narrow region 110, plus a second plurality of filaments braided into the first plurality of filaments. Narrow region 110 has greater flexibility than broader region 120, and, likewise, broader region 120 exhibits greater radial strength than narrow region 110.

FIG. 1B also shows transition region 130. Transition region is formed between narrow region 110 and broader region 120 and is comprised of the filaments which make up narrow region 110. Transition region 130 is formed during braiding on a mandrel of changing diameter, as described in more detail below.

The stents shown in FIGS. 1A and 1B are unitary stents. That is, the stent is one piece, unlike modular stent designs in which two or more stent segments are assembled together to form the various parts of the overall device (e.g., a trunk section and two legs). Thus, a unitary stent contemplates a stent whose entire length is made as a single unit, without the need to attach additional stent segments upon deployment. The stent as shown in FIG. 1B, for example, although unitary, exhibits different radial strengths along its longitudinal axis. This is because of the introduction of additional filaments in broader region 120.

It should be noted here that unitary stents 10 and 100 as shown in FIGS. 1A and 1B, respectively, are merely exemplary embodiments, and that this invention is applicable to "modular" braided stents as well. As used herein, the term "modular" means a stent having at least two discrete portions adapted for assembly in situ. As is well-known in the art, one type of exemplary modular stent may include a modular bifurcated stent comprising a trunk section with a bifurcated region that terminates in two short sockets into which two discrete leg members are adapted to be inserted. Although not depicted herein, such general configurations are well-known in the art. Thus, although the invention as illustrated and described herein primarily references a non-bifurcated structure, each of the methods and structures described herein is equally applicable to pieces of structures such as trunk components for receiving modular leg elements, which may themselves be made in accordance with the present invention.

Braiding of the filaments which form the stent of the present invention may be performed on a braiding machine having a predetermined plurality of bobbin carriers adapted to revolve in a pattern about a longitudinal axis. A first set of bobbin carriers may be adapted to revolve in a first circumferential direction and a second set of bobbin carriers may be adapted to revolve in a second circumferential direction, each bobbin carrier adapted to carry at least one bobbin. Each bobbin is adapted to provide one or more filaments for braiding the stent.

In such a case, braiding of the narrow, or flexible, region comprises using filaments from a first portion of the predetermined plurality of bobbins to braid the narrow portion about the first, narrow portion of the detachable mandrel leg positioned substantially along the longitudinal axis in a braiding zone. The braiding zone is defined as a conical zone defined by the filaments extending from the bobbins to the stent on the mandrel. The preferred number of filaments used to braid the narrow region is 12, although any suitable number may be used to achieve the desired balance between compressibility and radial strength of this region. The filaments used with the present invention may be any known to those skilled in the art, and preferably may be wire, such as nitinol or stainless steel, or may comprise a polymer.

In braiding the broader, or more rigid, region, the process comprises adding filaments from a second portion of the predetermined plurality of bobbins to increase the number of filaments used to braid the broader region about the second portion of the detachable mandrel leg positioned in the braiding zone. The additional filaments added are used in conjunction with the filaments already in place from braiding the narrow region of the stent. In other words, this second step comprises using filaments from both portions of the predetermined plurality of bobbins to braid the body about the second, larger diameter, mandrel body positioned in the braiding zone. The second plurality of filaments is only used in the broader region, and nowhere else in the stent.

Figure 2:
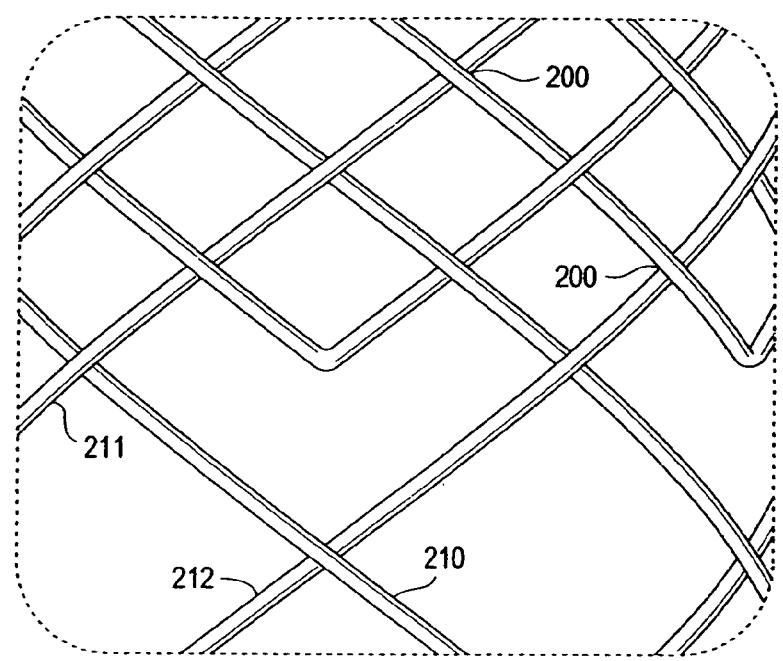
FIG. 2 is a close-up, partial view of an area of the stent of FIG. 1A or 1B between the flexible region and the rigid region.

FIG. 2 shows a flattened, partial view of an area of the stent 10 of FIG. 1A between flexible region 11 and rigid region 12, or the lower part of broader region 120 of stent 100 shown in FIG. 1B. This part of the stent according to the present invention, with reference to filaments 200, 210, 211, and 212, is discussed in more detail below. At each overlap, one filament is positioned radially outward relative to the other filament. Following each filament along its helical path through a series of consecutive overlaps, that filament may, for example be in the radial inward position in one overlap and in the radial outward position in a next overlap, or may in the inward position for two overlaps and in the outward position for the next two, and so on. As mentioned above, exemplary braided stents are disclosed in U.S. Pat. No. 4,655,771 to Hans I. Wallsten. A typical braided stent is formed on a mandrel by a braiding or plaiting machine, such as a standard braiding machine known in the art and manufactured by Rotek of Ormond Beach, Fla. Any such braiding or plaiting machine may be used, however, and the use of terminology specific to components of the machine manufactured by Rotek is not intended as a limitation to the use of that machine design. To the extent that the terminology used herein is specific to the components of any one or several machines, it should be understood such components specifically referred to herein generally have corresponding functionally equivalent components with respect to other machines. Thus, the scope of the method described and claimed herein for braiding the stent of the present invention is not intended to be limited to the specific machine embodiment described herein, but extends to functionally equivalent machines as well.

Figure 3:
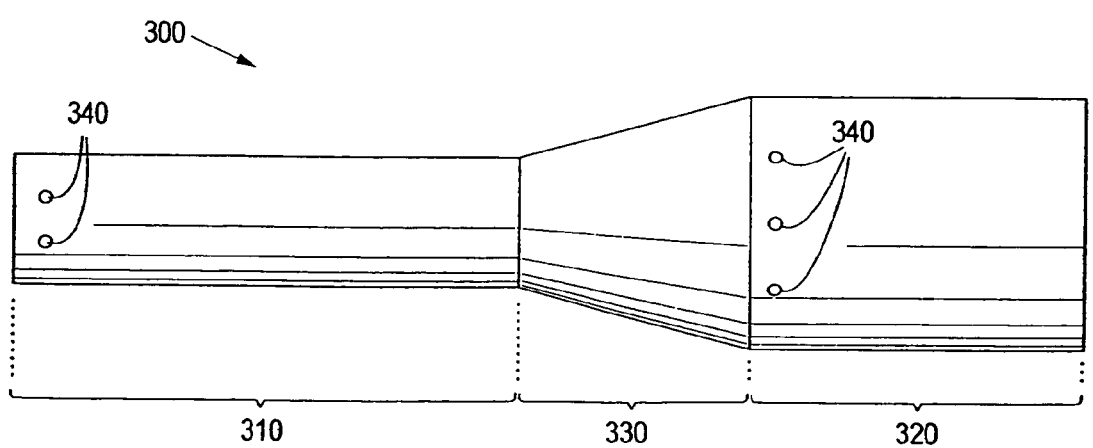
FIG. 3 is a side view of a mandrel used in accordance with the present invention to make the stent shown in FIG. 1B.

Braiding machines can be used for manufacturing the stent of the present invention about an exemplary modular mandrel as shown in FIG. 3. In FIG. 3, mandrel 300 comprises lower region 310 and upper region 320, with transition region 330 disposed therebetween. These regions correspond with the narrow region, broader region, and transition region, respectively, as shown in FIG. 1B. Pins 340 are also shown. Pins 340 are used to anchor filaments during braiding, an aspect known to those skilled in the art and discussed in more detail below.

Figure 4:
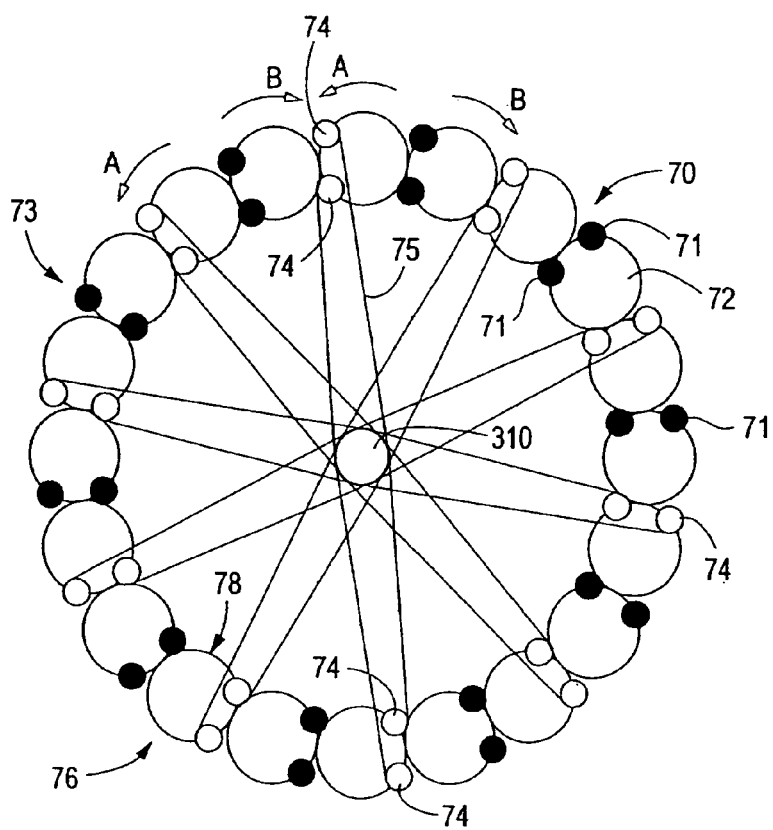
FIG. 4 is a front view of part of a braiding machine used to braid the narrow region of the stent shown in FIG. 1B.
Figure 5:
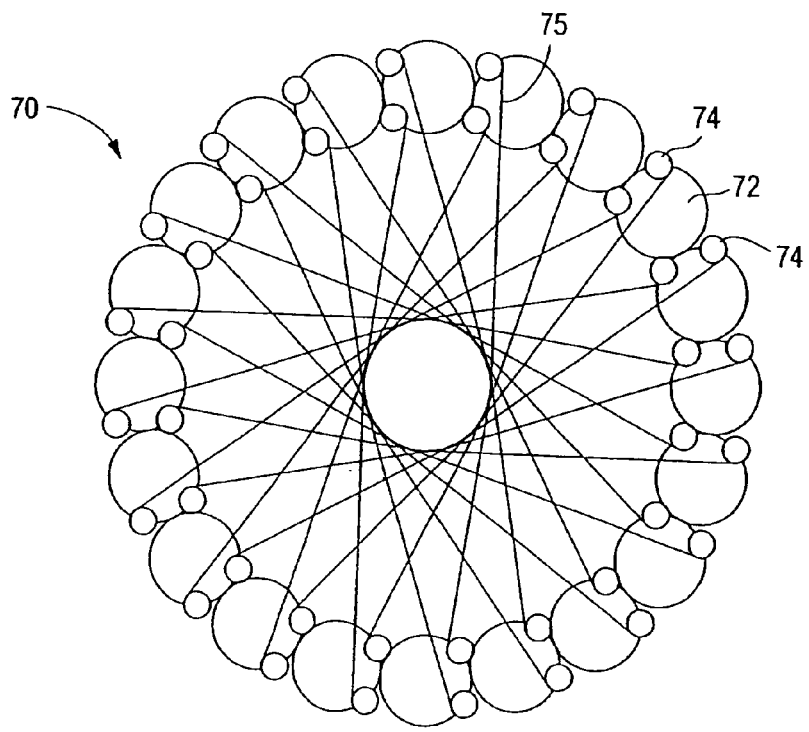
FIG. 5 is a front view of part of a braiding machine used to braid the broader region of the stent shown in FIG. 1B.

Referring now to FIGS. 4 and 5, braiding machine 70 is shown schematically as typically comprising a number of notch gears 72 arranged in a circle. Machine 70 shown in FIGS. 4 and 5 has twenty such notch gears 72, each notch gear adapted to rotate in the opposite direction as its neighboring notch gears, as illustrated by arrows A and B. This counter-rotation passes bobbin carriers 71, and the bobbins 74 mounted thereon, in a sinusoidal fashion from gear to gear, thus causing the bobbins to revolve about a longitudinal axis on which the circle is centered. The configuration of the notch gears, bobbin carriers, and bobbins to achieve this movement are well-known in the art, and an example of such a configuration is found in the braiding machine manufactured by Rotek.

Each bobbin comprises filament 75 wound thereon. The bobbin carrier and bobbin typically interface in a way that helps keep the wire unraveling from the bobbin under proper tension, as is known in the art. Although the motion of the bobbins is described herein, it should be understood that the bobbins 74 are moved by virtue of being mounted on bobbin carriers 71. Thus, although empty bobbin carriers 71 are shown in FIG. 4 (as darkened circles having no filament extending therefrom), each bobbin 74 also is mounted upon a bobbin carrier, creating a "loaded" bobbin carrier. To reduce clutter in FIGS. 4 and 5, the underlying bobbin carrier is not shown for carriers loaded with bobbins 74.

Figure 6:
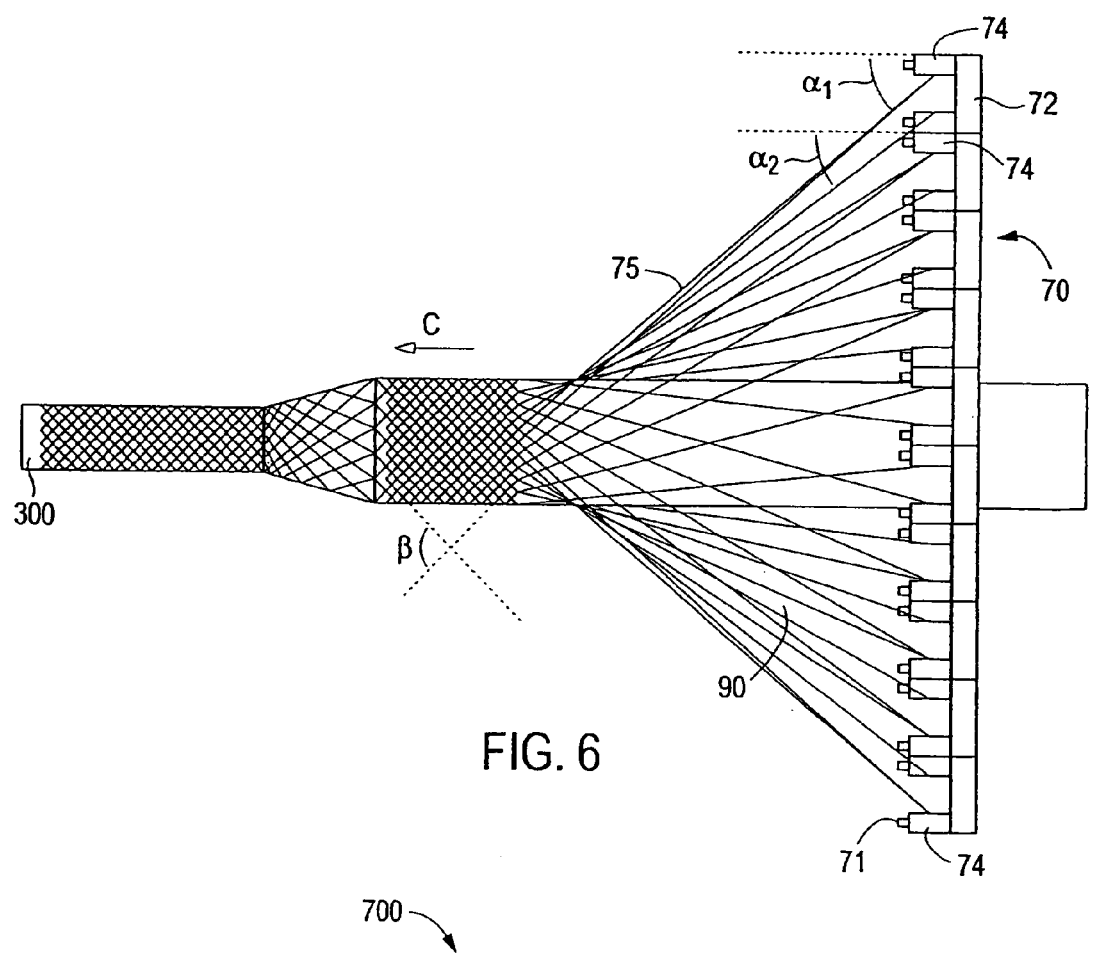
FIG. 6 is a side view of part of a braiding machine used to braid the stent shown in FIG. 1B.

During braiding, the mandrel around which braided stent 100 is formed, such as mandrel 300 as shown in FIG. 3, is moved in a controlled manner substantially along a longitudinal axis about which the circle of notch gears 72 is centered and about which the bobbin carriers 71 revolve. FIG. 6 illustrates, from the side, such a configuration. Thus, during braiding, wires 75 extend from braiding machine 70 to mandrel 300 in a conical configuration, as shown in FIG. 6.

As can be seen from FIG. 6, as two bobbins cross one another, their respective filaments form an overlap such that the filament from the bobbin on the outer radius 76 is disposed radially outward (with respect to the axis of the stent being assembled) relative to the filament from the bobbin on the inner radius 78. The space contained within the cone formed by the wires extending between the bobbins and the mandrel and including the space occupied by the mandrel is referred to herein as the "braiding zone" 90. Although the angles $\alpha_1$ and $\alpha_2$ of the wire to the mandrel may be varied as desired, $\alpha_1$ and $\alpha_2$ preferably each comprise an angle of approximately 55° when the braiding angle of a braided stent $\beta$ is approximately 110°. This angle may vary dependent upon the exact radial position of the bobbin relative to the mandrel and whether the wire is on the inside radial position or outside radial position on an overlap. As used herein, the phrase "substantially along the longitudinal axis" as used with respect to the alignment of the moving mandrel means that the mandrel does not have to be perfectly centered in the braiding zone, but merely needs to be aligned close enough to the longitudinal axis C that the angles of the filaments between the mandrel and the bobbins allows the braiding operation to create a functional braid without tangling the filaments.

To form a braid around a mandrel, wires 75 extending from bobbins 74 can be secured to the end of the mandrel in almost any manner, such as by taping them or tying them, and specifically do not have to be kept in any particular orientation. For example, all the wires may all be taped or tied to a single point on one side of the mandrel. Once the braiding machine starts, it will stabilize into the proper braid configuration after only a few circumferential hoops of overlaps are formed. The portion between the proper configuration and the end can either be cut away as scrap or unbraided and then manipulated to form a non-braided end winding, as is discussed herein below. In the alternative, to minimize scrap, the ends of wires 75 may be wound around pins (not shown) or otherwise secured to the mandrel in a spaced circumferential configuration similar to the configuration of bobbins 74 in braiding machine 70.

In a preferred embodiment, each filament has each of its two halves wound around a separate bobbin so that the filament is wound on to two bobbins, each half of the filament on a separate bobbin. In such a case, a first end of the filament is wound on a first respective bobbin and a second end of the filament is wound on a second respective bobbin, with the filament midpoint exposed between the two bobbins. From this pair of bobbins, the midpoint of the filament is withdrawn and positioned on the mandrel to form an apex at a point where each filament is added to the stent. It is not required that the exact midpoint be exposed between the two bobbins, only that the filament is wound generally equivalently on to each bobbin such that enough of the filament exists on each bobbin to allow braiding of the stent.

For example, if a stent is desired such as that shown in FIG. 1B, six pairs of bobbins are prepared and disposed on a braiding machine as described in more detail below. Each apex 140, for a total of 6 apices, is formed by attaching the approximate midpoint of each filament to the mandrel. With 12 bobbins thus disposed to provide 12 wires to braid (one "wire" extending in opposing directions from each of six apices 140), narrow region 110 is braided. In such a case, although actually six filaments are used, the narrow region is effectively braided with 12 wires because each filament bends at apex 140. Then, once narrow region 110 and transition region 130 are braided, an additional six pairs of bobbins are added, with six apices 150 formed at the beginning of broader region 120. Thus, broader region 120, as shown, is effectively braided of 24 wires. The apices described above are preferably formed by winding each filament about a respective pin on the mandrel as is well known in the art. Each such pin is the point where an apex is formed.

In such a case as just described, the first and second bobbins should be positioned on bobbin carriers in positions consistent with the helical angle of the stent and the distance of the mandrel from the bobbin carriers. Thus, the first and second bobbins may be positioned at opposite ends of a radius of the circle of notch gears, or at opposite ends of some chord through the circle, depending on the exact configuration of the machine and desired helical angle of the stent. An exemplary process for providing a stent with such ends is described in publication WO 99/25271 to Burlakov et al. and is incorporated herein by reference.

In one method for creating the braided stent of the present invention, the braiding machine is first loaded as shown in FIG. 4 with a first portion 73 of a predetermined number of bobbins 74. The predetermined number of bobbins may comprise the maximum capacity of the machine. In such a case, a different machine, with at least twice the number of bobbin carriers, would have to be used for braiding the broader region. Alternatively, the first portion 73 may comprise half of the bobbin capacity of the machine. This latter embodiment is that which is shown in FIG. 4, in which 10 of the 20 available bobbin carriers are loaded and ready for braiding.

The braiding operation is then performed as described above to form the narrow region of the braided stent around lower region 310 of mandrel 300. After braiding the narrow region about the lower region of the mandrel, and the transition region of the stent about the transition region of the mandrel, the stent is ready to have the additional filaments added so that the additional filaments can join the existing filaments and together form broader region 120 around upper region 320 of the mandrel.

Where the bobbins used to braid narrow region 110 must be moved from the braiding machine as described in more detail below, the existing filaments which are going to be used to finish braiding the stent must be secured to prevent backlashing or loosening of that part of the stent already braided. This can be done either by tying each off on a pin on the mandrel, or simply tying or clamping all of the filaments against the mandrel at a point where the additional filaments are going to be added to form the broader region of the stent.

As noted above, the method for adding filaments in preparation of braiding the broader region may include moving the bobbins used in the braiding of the narrow region. This movement may be accomplished by any of a number of ways. For example, certain bobbin carriers may comprise closed eyelets through which the wire is threaded, in which case the entire bobbin carrier may be removed. Other bobbin carriers, such as those manufactured, for example, by the Wardwell Braiding Machine Company of Central Falls, R.I. comprise open, curled guides resembling a "pigtail" such that the bobbins may be simply unlocked and lifted off of their respective bobbin carriers and the filament readily removed from the guide. It should be understood that, as referred to herein, removing or replacing "the bobbins" on and off of the machine may comprise removing or replacing the bobbins only or the bobbins as still attached to the bobbin carriers. Where the entire bobbin carrier is removed, the bobbin carrier may be removed by simply removing any fasteners holding it in place, or to facilitate quicker removal and replacement, a quick-connect fitting can be used. The quick-connect fitting may comprise any number of means well-known in the art for providing an interlocking engagement of one element with another, such as a magnetic connection, a twist-and-lock connection, a spring-loaded ball in channel connection, a lever-controlled cam connection, or any connection known in the art.

The filament addition process can be essentially understood by comparing FIGS. 4 and 5. Prior to filament addition, the bobbins are configured as shown in FIG. 5, with pairs of bobbins positioned relative to one another shown with empty bobbin holders between each pair. To prepare to braid the broader region of the stent in one embodiment, additional bobbin pairs are added between each bobbin pair used to braid the narrow region.

Alternatively, if the bobbin machine used to braid the narrow region of the stent has no additional bobbin holders (a situation not shown in FIG. 4), the system of bobbin pairs and mandrel used to braid the narrow region and transition region can be moved to a machine which has at least twice the number of bobbin carriers. During the bobbin movement step in such a case, it is desirable to preserve the clockwise or counter-clockwise rotation of each bobbin 74. Bobbin carriers 71 can be said to form a first set of bobbin carriers that traverse the circle of notch gears 72 in the counter-clockwise direction, whereas bobbin carriers 71 form a second set of bobbin carriers that traverse the circle in the clockwise direction. Furthermore, where the entire bobbin carrier is removed, it is desirable for the bobbin carrier to be replaced in a position where it travels in the same direction as it traveled prior to removal.

Important in the filament addition step is that the bobbins be arranged, either by movement to a different machine, or addition of extra bobbins, so that the desired overlap between filaments be obtained. For example, and as shown in FIG. 2, the general pattern is under/over/under/over through the length of the filament. Certain regions, however, such as for filament 210 in transition region 130, will have the filament, such as filament 210, disposed under to consecutive parallel filaments 211 and 212. The preferred arrangement of the braiding can vary, and is generally known by those skilled in the art. So long as a desired pattern is known, the bobbins can be arranged when the filaments are added for the broader region so as to achieve that desired pattern.

With regard again to FIGS. 4 and 5, the counter rotation of the notch gears means that each notch gear 72 having a clockwise-rotating bobbin 74 on outer radius 76 has neighboring notch gears on either side with the clockwise-rotating bobbin on inner radius 78. In an alternate embodiment, bobbin carriers 71 (and therefore bobbins 74) may travel clockwise instead of counter-clockwise, with carriers 71 and bobbins 74 travelling counter-clockwise. It may be preferable, however, for the tangent of the wire to the bobbin to be on the same side of the bobbin as on the mandrel so that the wire is wound on the same helical direction on the mandrel as it was on the bobbin. For example, as shown in FIG. 4, the wire originating from bobbin 74 is tangent to the right side of both the bobbin and mandrel 300, and likewise the wire originating from bobbin 74 is tangent to the left side of both the bobbin and mandrel.

Figure 7:
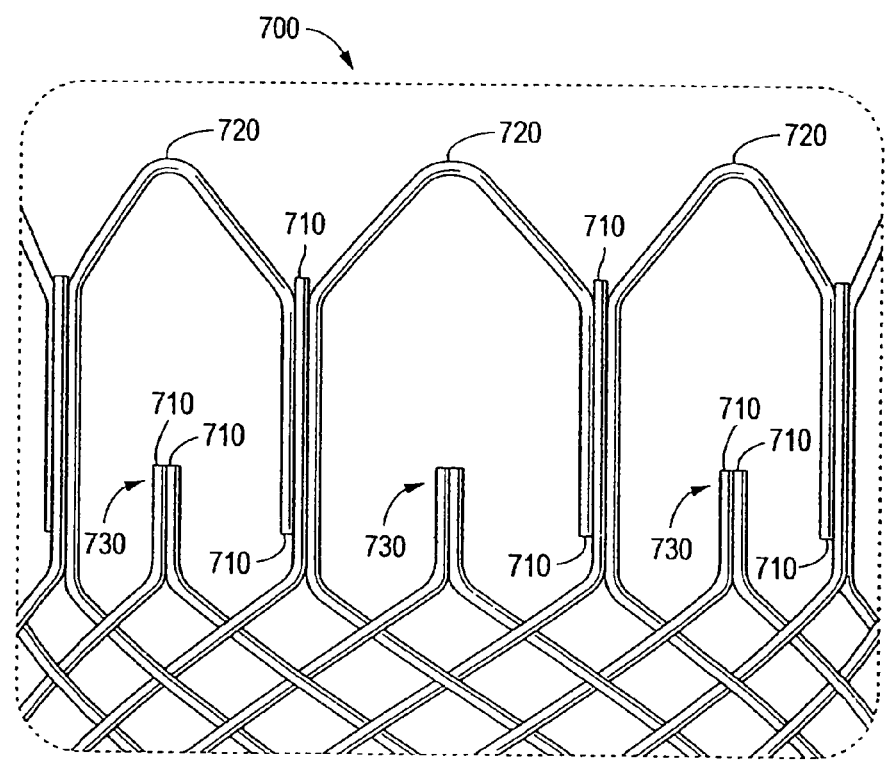
FIG. 7 is a close-up, partial view of an atraumatic end of a stent in accordance with the present invention.

To provide increased radial strength at the ends of the braided stent of this invention or to counteract a known end-effect of braided stent architecture where the ends tend to have lesser radial strength than the intermediate portion of the stent, the ends may be flared as is well known in the art, or the ends may comprise a non-braided stent architecture such as is shown in FIG. 7. The structure and method for making a hexagonal non-braided architecture 700 with an overlapping end winding 710 shown in FIG. 7 can be accomplished through known winding and welding techniques. In the embodiment shown in FIG. 7, each filament end 710 is welded to an adjacent piece of filament near its end 710. Apices 720 are formed to make the end of the stent "atraumatic." Shorter filament segments terminating below apices 720 may be otherwise-terminated, such as by clipping them at otherwise-terminated free ends 730. The end architecture as shown in FIG. 7 can be described as "atraumatic" in the sense that there are no loose or sharp wire ends that may puncture or irritate (or otherwise cause trauma to) the lumen wall after implantation. Other methods of providing atraumatic ends may also be used as are known in the art. The end architecture is not limited to the architecture shown and described above, but may comprise any number of configurations known in the art.

Atraumatic ends of the braided stent structure may also be provided by making adjacent filament pairs of filaments from each of the angularly disposed sets of parallel filaments, continuous with one another. Such atraumatic ends may be located at an end of the stent, as seen at 140 in FIG. 1B, or at the mid-stent end of a stent region as seen at 150 in FIG. 1B, where an additional plurality of braided filaments are continuous with one another.

Moreover, using the method described above, one end of the stent has atraumatic, continuous-wire apices 140 such as are shown in FIG. 1B at the end of the narrow region 110. The filaments on the opposite end are preferably also atraumatically disposed ends in a non-braided architecture, such as for example apices 720 shown in FIG. 7. These are only examples, however, as the free ends may terminate in any way known in the art. Although one end of a stent may have some combination of continuous-wire apices 720 and otherwise-terminated free ends 730, the preferred embodiment comprises one end of the stent having only continuous-wire apices 720.

To deploy the stent of this invention, the stent is typically compressed into a radially compressed state into an introducer as is well-known in the art. The stent is then introduced to the lumen into which it is to be deployed, navigated through the lumen to a deployment location, typically a diseased artery such as the aorta, and then expanded to a radially expanded state in the deployment location as is known in the art. The deployment of a unitary stent of the present invention is thus accomplished by a method similar to that used for any stent known in the art. Expansion is also achieved through known methods (e.g. the stent is expandable between the radially compressed configuration and the radially expanded configuration by one of: balloon expansion, self-expansion via spring elasticity, or self-expansion via a thermally or stress-induced return of a pre-conditioned memory material).

Although non-bifurcated stent designs have been shown and described herein, the method of the present invention may be used for creating stent segments which are combined to form bifurcated systems or any number of multiple lumen systems.

Figure 1C:
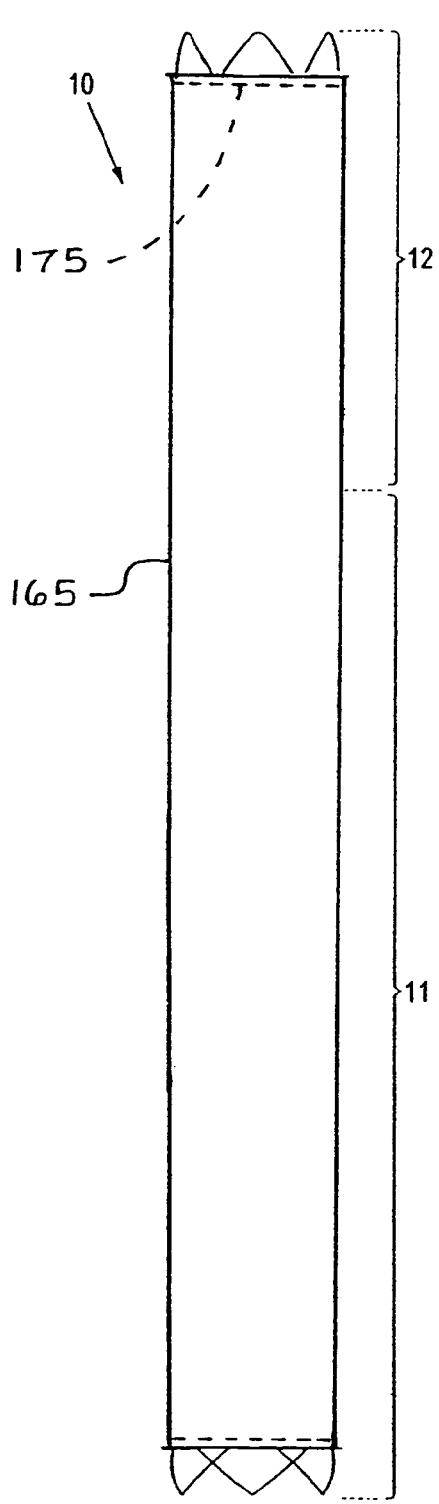
FIG. 1C is the stent as shown in FIG. 1A but includes both a graft outer covering and an inner liner.
Figure 1D:
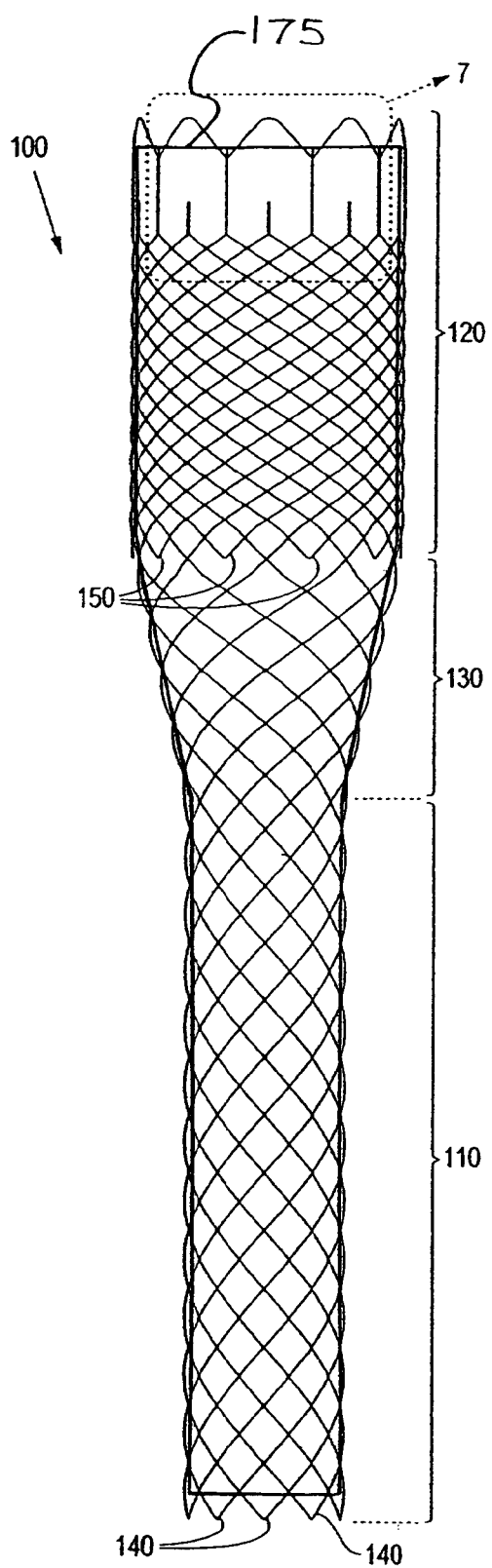
FIG. 1D shows a stent according to the present invention which has an inner lining.

The stent of the present invention can also be used with any biocompatible graft connected thereto as one of: an outer covering 165, an inner liner 175, or a combination thereof (as shown in FIGS. 1C and 1D). These grafts are known to those skilled in the art. As used herein, the term, "stent" is intended to generally refer to a wire support frame alone, or a wire support frame in conjunction with a graft material connected thereto as one of: an outer covering, an inner liner, or a combination thereof. This later stent is sometimes referred to as a "stent-graft" or "prosthesis comprised of a stent and graft."

While described above with reference to embodiments having only two regions of differential properties, stents or stent-grafts with three or more regions of differential properties are also envisioned and may also be made by duplicating the teaching above for introducing and terminating a separate plurality of filaments at a mid-stent location.

Note too that the differential properties provided by varying the number of filaments in a braided stent structure are not limited to dimensional or rigidity/flexibility/strength characteristics, but may also include other properties, such as magnetizability, imagability, space density (the proportion of stent circumference occupied or not occupied by filaments), etc.

Although illustrated and described above with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A tubular stent comprising:
    a plurality of filaments extending throughout a length and interbraided to define a tubular, supportive structure having a longitudinal axis, each filament having a filament length, opposed filament ends and a filament midpoint between the opposed filament ends;
    a first atraumatic end integral with said tubular structure; and
    a second atraumatic end integral with said tubular structure and opposed from the first atraumatic end to define a tubular stent;
    wherein the first atraumatic end of said stent comprises bends at about the midpoints of said plurality of filaments forming first apices thereat to define said first atraumatic end;
    wherein the second atraumatic end of said stent comprises filament wound architectures having second apices formed from bends in a portion of said plurality of filaments;
    wherein the filament wound architectures consist essentially of non-braided architectures; and
    wherein the filament ends are disposed proximally away from said second apices.

2. The stent of claim 1, wherein the filament wound architectures consist of non-braided, hexagonal architectures.

3. The stent of claim 1, wherein the filaments comprise wires.

4. The stent of claim 3, wherein said wires are selected from the group consisting of nitinol, stainless steel or combinations thereof.

5. The stent of claim 1, wherein said plurality of filaments have a braiding angle along the longitudinal axis.

6. The stent of claim 5, wherein said braiding angle is obtuse.

7. The stent of claim 6, wherein said braiding angle is about 110°.

8. The stent of claim 1, wherein said plurality of filaments vary from about 6 filaments to about 12 filaments.

9. The stent of claim 1, wherein the stent has a radially compressed configuration for introduction into the lumen and a radially expanded configuration for deployment within the lumen.

10. The stent of claim 9, wherein the stent is expandable between the radially compressed configuration and the radially expanded configuration by one of balloon expansion, self-expansion via spring elasticity, or self-expansion via a thermally or stress-induced return of a pre-conditioned memory material.

11. The stent of claim 1, further comprising a biocompatible tubular graft, said graft comprising an outer covering, an inner liner, or a combination thereof, for at least a portion of said stent.

12. A method of constructing a braided stent, comprising:
providing a mandrel;
providing a plurality of filaments;
winding each filament between two bobbins such that a first end of each filament is wound on a first respective bobbin and a second end of each filament is wound on a second respective bobbin;
positioning a point of each filament on the mandrel to form an apex to define a first atraumatic end of a braided stent;
braiding the plurality of filaments to form a lengthwise region of the braided stent; and
winding a portion of the plurality of filaments to form apices in the wound filaments to define a second atraumatic end of the braided stent;
wherein the portion of the plurality of filaments are wound essentially in a non-braided architecture to form the apices at the second atraumatic end of the braided stent.

13. The method of claim 12, further comprising:
disposing the filament ends proximally away from said second apices.

14. The method of claim 12, wherein the filaments comprise wires.

15. The method of claim 14, wherein said wires are selected from the group consisting of nitinol, stainless steel or combinations thereof.

16. The method of claim 12, further comprising
braiding said plurality of filaments at a braiding angle along the lengthwise region.

17. The method of claim 16, wherein said braiding angle is obtuse.

18. The method of claim 16, wherein said braiding angle is about 110°.

19. The method of claim 12, wherein said plurality of filaments vary from about 6 filaments to about 12 filaments.

20. The method of claim 12, further comprising:
performing the braiding on a braiding machine having a predetermined plurality of bobbins adapted to revolve about a longitudinal axis, a first set of bobbins adapted to revolve in a first circumferential direction and a second set of bobbins adapted to revolve in a second circumferential direction, each bobbin mounted upon a bobbin carrier adapted to carry at least one bobbin, and each bobbin adapted to provide one or more filaments for braiding into the stent.

21. The method of claim 12, wherein the wound portion of the plurality of filaments consist of a non-braided, hexagonal architecture.

* * * * *